United States Patent [19]

Kaplan

[11] Patent Number: 5,342,348

[45] Date of Patent: Aug. 30, 1994

[54] METHOD AND DEVICE FOR TREATING AND ENLARGING BODY LUMENS

[76] Inventor: Aaron V. Kaplan, 3477 Thomas Dr., Palo Alto, Calif. 94303

[21] Appl. No.: 985,382

[22] Filed: Dec. 4, 1992

[51] Int. Cl.$^5$ .............................................. A61K 9/22
[52] U.S. Cl. ................................. 604/891.1; 623/13; 606/198; 604/28
[58] Field of Search ................ 604/96, 97, 104, 132, 604/133, 891.1; 606/191, 198; 623/1, 11, 12, 13, 900

[56] References Cited

U.S. PATENT DOCUMENTS

| | | |
|---|---|---|
| 4,300,244 | 11/1981 | Bokros . |
| 4,580,568 | 4/1986 | Gianturco . |
| 4,733,665 | 3/1988 | Palmaz . |
| 4,739,762 | 4/1988 | Palmaz . |
| 4,776,337 | 10/1988 | Palmaz . |
| 4,800,882 | 1/1989 | Gianturco . |
| 4,834,755 | 5/1989 | Silvestrini et al. ............... 623/13 |
| 4,990,155 | 2/1991 | Wilkoff . |
| 5,019,090 | 5/1991 | Pinchuk . |
| 5,053,048 | 10/1991 | Pinchuk ........................... 623/1 |
| 5,059,211 | 10/1991 | Stack et al. ..................... 606/198 |
| 5,234,456 | 8/1993 | Silvestrini ....................... 604/194 |

FOREIGN PATENT DOCUMENTS

| | | |
|---|---|---|
| 0281482 | 9/1988 | European Pat. Off. . |
| 0433011 | 6/1991 | European Pat. Off. . |
| 87/04935 | 8/1987 | World Int. Prop. O. . |
| 9117789 | 11/1991 | World Int. Prop. O. ......... 606/198 |
| 92/11890 | 7/1992 | World Int. Prop. O. . |
| 92/11895 | 7/1992 | World Int. Prop. O. . |

OTHER PUBLICATIONS

Chasin et al. "Polyanhydrides as Drug Delivery Systems" in Biodegradable Polymers . . . , Mercel Dekker 1990 pp. 43–70.
Langer (1990) Science 249:1527–1532.
Langer and Moses (1991) J. Cell. Biochem. 45:340–345.

*Primary Examiner*—C. Fred Rosenbaum
*Assistant Examiner*—Vanitha Alexander
*Attorney, Agent, or Firm*—Townsend and Townsend Khourie and Crew

[57] ABSTRACT

The present invention relates generally to stents having delivery matrices which provide for the controlled release of bioactive substances. The delivery matrices comprise porous and erodible filaments, and multiple filaments may be employed in order to release different bioactive substances and/or the same bioactive substance at different delivery rates. The stents are particularly useful for preventing restenosis of dilated body lumens, such as blood vessels. Methods for preventing stenosis of dilated body lumens or locally delivering bioactive compounds to tissue are also provided.

24 Claims, 6 Drawing Sheets

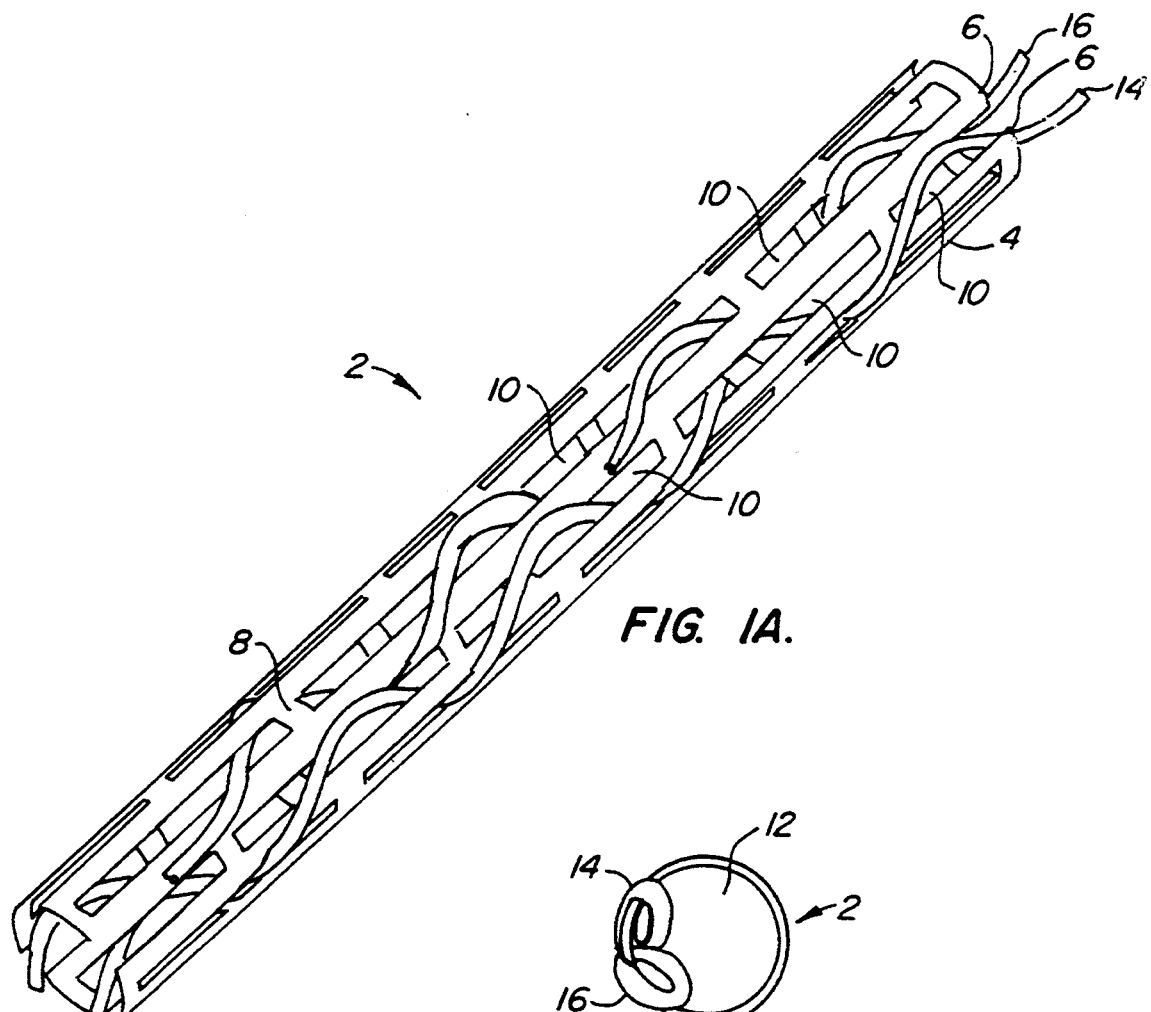
FIG. 1A.
FIG. 1B.
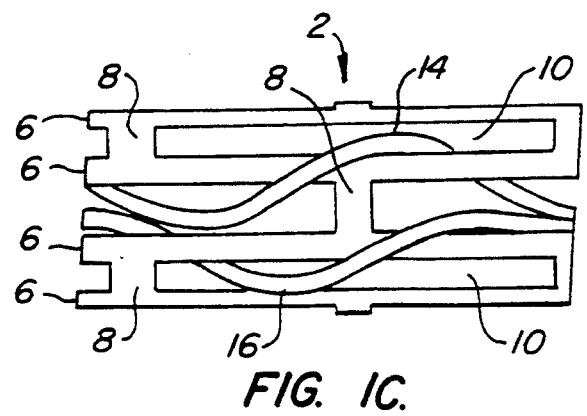
FIG. 1C.

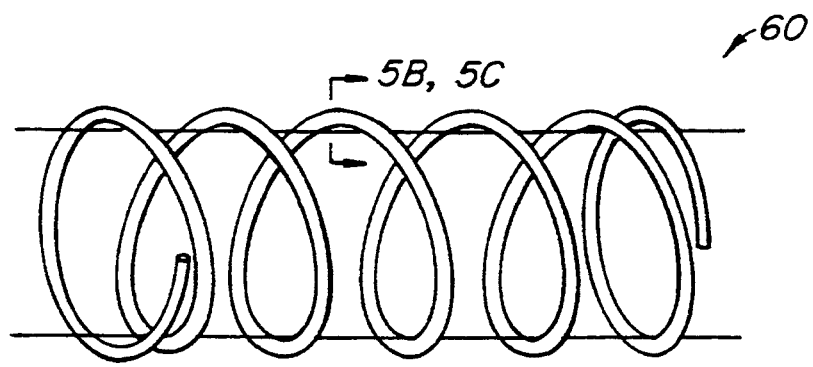
FIG. 5A.
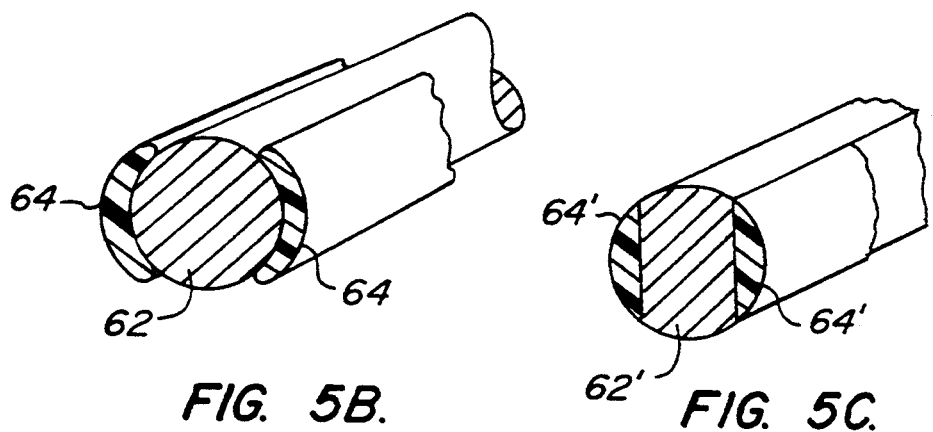
FIG. 5B.
FIG. 5C.

METHOD AND DEVICE FOR TREATING AND ENLARGING BODY LUMENS

BACKGROUND OF THE INVENTION

1. Field of the Invention

The present invention relates generally to intraluminal stents. More particularly, the present invention provides devices and methods which allow for localized delivery of bioactive compounds.

Many diseases may cause body lumens to undergo stenosis. Probably the most common is atherosclerosis. Atherosclerosis is a condition which commonly affects the coronary arteries of the heart, the aorta, and the carotid arteries. Atherosclerotic plaques of lipids, fibroblasts, and fibrin proliferate and cause obstruction of the artery. As the obstruction increases, a critical level of stenosis is reached which does not allow sufficient blood flow to pass the obstruction to meet the metabolic needs of tissue distal to the obstruction resulting in ischemia. Atherosclerotic plaques also have the potential for rupture which can expose the flowing blood to a strong procoagulant stimuli often resulting in thrombus formation. Thrombus formation in the coronary circulation leads to unstable angina and myocardial infarction. Thrombus formation in the cerebral circulation leads to stroke, TIA (transient ischemic attack) and RIND (reversible ischemic neurologic deficit).

Many therapeutic alternatives are available for the treatment of atherosclerotic diseases, including surgery and medical treatment. One particularly useful therapy for selected atherosclerotic lesions is percutaneous transluminal angioplasty. During angioplasty, a balloon tipped catheter is inserted in an artery of the patient with the balloon deflated. The catheter tip is advanced to the site of the atherosclerotic plaque to be dilated. The balloon is placed within the stenotic segment of the artery and inflated. During inflation the plaque "cracks" and the vessel expands, at least partially relieving the stenosis.

While angioplasty has gained wide acceptance, it suffers from two major problems, i.e. abrupt closure and restenosis. Abrupt closure refers to the acute occlusion of a vessel immediately after or within the initial hours following a dilatation procedure. Abrupt closure occurs in approximately one in twenty cases and frequently results in myocardial infarction and death if blood flow is not restored in a timely manner. The primary mechanisms of abrupt closures are arterial dissection and/or thrombosis. It is postulated, that the ability to deliver agent (e.g. antithrombotic) directly into the arterial wall at the time of angioplasty could reduce the incidence thrombotic acute closure.

Restenosis refers to the re-narrowing of an artery after an initially successful angioplasty. Restenosis occurs within the initial six months after angioplasty and is due to the proliferation and migration of the cellular components of the arterial wall. It is postulate that the delivery of agent(s) directly into the arterial wall would interrupt the cellular events leading to restenosis.

Medical prevention of abrupt closure and restenosis has not been entirely successful. Endovascular stents have been placed in the dilated segments to mechanically block abrupt closure and restenosis. Unfortunately, such stents have a high rate of thrombotic abrupt closure and have not significantly reduced restenosis.

Non-atherosclerotic vascular stenosis may also be treated by angioplasty. For example, Takayasu arteritis or neurofibromatosis may cause stenosis by fibrotic thickening of the arterial wall. Restenosis of these lesions occurs at a high rate following angioplasty, however, due to the fibrotic nature of the diseases. Medical therapy has been similarly disappointing.

What is needed in the art are devices and methods for the prevention of abrupt closure and/or restenosis following dilation of blood vessels. In particular, it would be desirable to provide devices and methods which can provide antithrombic and other medications to regions of a blood vessel which have been treated by angioplasty or other interventional techniques, such as atherectomy, laser ablation, or the like. Such devices should be capable of providing both short term medication delivery, over the initial hours and days after the treatment, as well as long term medication delivery, over the weeks and months after the treatment. Surprisingly, the present invention fulfills these and other needs.

2. Description of the Background Art

U.S. Pat. No. 4,300,244 describes an endovascular prosthesis which may be coated with carbon for biocompatibility. U.S. Pat. No. 4,580,568 describes endovascular stents which are formed of stainless steel in a zig-zag pattern. U.S. Pat. No. 4,733,665 describes expandable intraluminal vascular grafts placed by balloon angioplasty catheters. U.S. Pat. No. 4,739,762 describes expandable intraluminal grafts which may have a plurality of slots in the graft walls. U.S. Pat. No. 4,776,337 describes expandable intraluminal stents coated with a biologically inert substance, such as polyurethane or other inert plastics. U.S. Pat. No. 4,800,882 describes an expandable endovascular stent formed from wire bent into serpentine configurations. U.S. Pat. No. 4,990,155 describes a plastic coil for use as an endovascular stent to prevent restenosis following angioplasty. U.S. Pat. No. 5,019,090 describes radially expandable endoprostheses. U.S. Pat. No. 5,053,048 describes thromboresistant coating which may be applied to intravascular stents. U.S. Pat. No. 5,059,211 describes expandable endovascular stents which are bioabsorbable. Each of the above references is incorporated herein by reference.

PCT Application No. 92/11895 describes a balloon catheter capable of releasing drugs directly to tissue in a body lumen wall. PCT Application No. WO 92/11890 describes a balloon catheter having a coating of body affecting chemicals which are released when the balloon is inflated and contacted with body lumen walls. PCT Application No WO 87/04935 describes spring coil intravascular stents. European Patent Publication No. 281,482 describes preparation of biodegradable polymers. European Patent Publication No. 433,011 describes an intra-arterial stent which incorporates or is coated with a radioisotope. Chasin et al., "Polyanhydrides as Drug Delivery Systems" in *Biodegradable Polymers as Drug Delivery Systems*, Langer and Chasin, eds., Mercel Dekker, Inc., 1990, pp. 43–70; Langer, *Science*, 249:1527–1532; and Langer and Moses, *J. Cell. Biochem.*, 45:340–345 describe biodegradable materials useful in drug delivery systems. Each of the above references is incorporated herein by reference.

SUMMARY OF THE INVENTION

The present invention provides endovascular stents and methods for delivering therapeutic and other substances to selected locations within a patient's vascular system. The endovascular stent comprises a tubular structure having an initial diameter and being expandable from the initial diameter to an enlarged diameter. A delivery matrix including at least one filament is interlaced with the tubular structure and expandable therewith from the initial diameter to the enlarged diameter. A bioactive substance is releasably contained within the filament of the delivery matrix, and is released from said matrix when exposed to the conditions present in the vascular system.

The tubular structure may be composed of an elastic material, such as an elastomer polymer, whereby the tubular structure may be initially constrained to set initial diameter and thereafter released to said enlarged diameter. Alternatively, the tubular structure could be composed of a non-plastic material, whereby the tubular structure may be expanded from the initial diameter to the enlarged diameter, typically using a balloon dilatation catheter. The various specific designs for the tubular structure exit, including a helical structure where the filament of the delivery matrix is counter woven with a helical strand of the tubular structure, a helical structure where the filament is laminated to a helically wound strand of the tubular structure, and a perforated cylinder where the filament of the delivery matrix is interwoven through perforations in the cylinder. The filament of the delivery matrix may be porous and substantially non-erodible, where the bioactive substance is absorbed or impregnated therein and released over time. Alternatively, the filament will be composed of the material which is erodible within the vascular environment, where the bioactive substance is contained or dispersed in the filament and released as the filament material erodes.

In a preferred embodiment of the endovascular stent, the delivery matrix will include at least one first filament and at least one second filament, where the first and second filaments are both interlaced with the tubular structure and expandable therewith. Usually, the first and second filaments will have differing characteristics so that the first filament will release a bioactive substance contained therein over a first time period and the second filament will release a bioactive substance contained therein over a second time period. In this way, a single bioactive substance can be delivered over two independent profiles, and/or two different bioactive substances may be delivered simultaneously or over different delivery profiles.

According to the method of the present invention, a stent is inserted into a body lumen to delivery a bioactive substance. The stent is constructed as described above and is expanded at a location within the body lumen selected to be treated. After such placement, the bioactive substance(s) are released according to the mechanisms described above.

BRIEF DESCRIPTION OF THE FIGURES

FIG. 1A illustrates a perspective view of a stent prior to expansion having two stands woven through the perforations.

FIG. 1B illustrates a view through the interior of a stent prior to expansion having two strands woven through the perforations.

FIG. 1C illustrates a close-up perspective view of a stent having two strands woven through the perforations prior to expansion.

FIG. 5A is a side elevational view of a stent comprising a single helically wound strand having a pair of delivery matrix filaments laminated thereto.

FIG. 5B is a detailed cross-sectional view illustrating a first configuration for laminating the filaments onto the strand of FIG. 5A.

FIG. 5C is a detailed cross-sectional view illustrating a second configuration for laminating the filaments onto the strand of FIG. 5A.

DETAILED DESCRIPTION OF THE SPECIFIC EMBODIMENTS

Figure 2B:
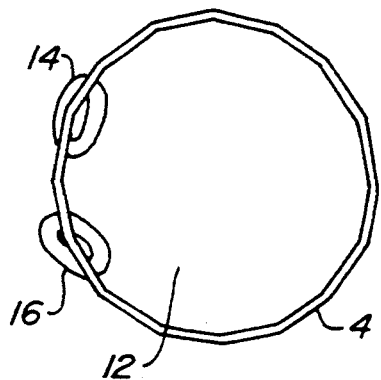
FIG. 2B illustrates a view through the interior of a stent following expansion having two strands woven through the perforations.

The present invention provides devices and methods for treating body lumens particularly for preventing restenosis of blood vessels following dilation of stenotic segments. The devices and methods also provide a means for delivering bioactive substances and compounds in a localized manner.

According to the present invention, an endovascular stent comprises a tubular structure having an initial diameter and being expandable from the initial diameter to an enlarged diameter. For most vascular applications, the initial diameter will be in the range from about 1.25 mm to 2 mm, usually being from about 1.25 mm to 1.5 mm. The final enlarged diameter will usually be in the range from about 2 mm to 6 mm, more usually being from 2 mm to 4 mm. The tubular structure can have any of a variety of conventional stent structures, such as helically wound strands, perforated cylinders or the like. The number of specific structures are disclosed in the background patents which are listed above and which have been incorporated herein by reference.

Endovascular stent will further comprise a delivery matrix for containing and releasing a bioactive substance into the body lumen being treated, typically a blood vessel. The delivery matrix will include at least one filament which is interlaced with the tubular structure which is expandable therewith from the initial diameter to the enlarged diameter. It will be appreciated that the tubular structure acts as a mechanical support for the delivery matrix, thus allowing a wide variety of materials to be utilized as the delivery matrix.

By "bioactive substance", it is meant that the compound exerts a biological effect on the tissue of the host. The biological effect will generally be local in nature, i.e. only occurring very close to the strand, but may also exert biological effects more distantly. The biological effects may include anti-proliferative activity, thrombotic inhibition, inhibition of vasospasm, or the like.

The tubular structure may be composed of a variety of bio-compatible materials. Typically, the tubular member may be stainless steel; silver; tantalum; gold; titanium; tungsten; platinum; polymers, such as polyether sulfone, polyamide, polycarbonate, polypropylene, high molecular weight polyethylene; carbon fiber; and the like. When the tubular member is constructed of radiolucent materials, such as polypropylene or polyethylene, a radiopaque coating may be applied to the stent. The radiopaque coating provides a means for identifying the location of the stent by plain x-rays or fluorography during or after stent placement.

The tubular structure will generally have non-elastic (plastic) properties in that it will retain its shape following expansion. This provides a means for controlled expansion in the body lumen. In these embodiments, an outward force applied from the interior of the stent will increase the diameter of the tubular member. The degree of radial expansion can be controlled by the amount of force exerted. Angioplasty balloon catheters provide a means for controlling the force, and hence the expansion, of the tubular member. The catheter balloon can be expanded to predetermined pressures in order to expand the tubular member.

Alternatively, the tubular structure can have elastic properties. In these embodiments, the tubular member is held in a contracted position for placement. Outward tension is created in the tubular member by the force contraction. When the stent is placed, the tension within the tubular member causes expansion of the tubular member. The tubular member expands to securely contact the lumen wall.

The tubular structure may be coated with a biologically inert coating. Examples of suitable inert coatings include porous polyurethane, Teflon ®, or other conventional biologically inert plastic substances. The coating should be thin and highly elastic so as not to interfere with expansion of the stent. The coating may also have anchoring means for securing the stent to the inner wall of the body lumen. The anchoring means may be projections which extend radially outward from the outer surface of the tubular member.

In a first exemplary embodiment, the tubular structure will be a perforated cylinder. The perforations in the cylinder may be circular, ovoid, slots, or the like. The tubular structure may also be comprised of a helically wound or serpentine type wire structure. The turns or curves in the wire are analogous to the perforations in the perforated cylinder, as described below.

The perforations or open wire structure will permit expansion of the tubular structure. The solid portions of the perforated cylinder may be deformed by outward expanding forces from within the tubular member. While the perforations allow deformation of the solid portions of the tubular member, the tubular member will retain the expanded shape following deformation under the naturally occurring forces within the body lumen.

The perforations may be formed in cylindrical members by etching or cutting through the solid walls. Conventional etching processes such as electromechanical or laser etching may be used. Alternatively, the tubular members may be constructed from a plurality of longitudinal members joined to form a tubular structure. The longitudinal members may be joined by welding, soldering, brazing, or epoxy resins, depending on the composition of the longitudinal members. The longitudinal members will generally have a circular cross-sectional shape, but may also have a cross-sectional shape which is triangular, square, rectangular, and the like. Horizontal members may also be employed to join the longitudinal members by similar means. By joining the longitudinal members at discrete points along their length, perforations are formed in the tubular member.

The perforations also provide a means for immobilizing the filaments of the delivery matrix in the tubular structure. The filaments contain bioactive compounds which are released in a controlled fashion following placement of the stent. By interlacing the filament through the perforations of the tubular structure, the filaments are held in close contact with the wall of the body lumen by the expanded tubular member.

Generally, the filaments are polymers which are degradable over time, within the vascular environment. By "biodegradable polymer," it is meant that the polymer will naturally erode in a physiological environment. The bioactive compounds are mixed in the polymer and released as the polymer degrades. Polymers may be synthesized with specific degradation characteristics determining the life span of the polymer under physiological conditions. The rate of polymer degradation and the concentration of bioactive compound in the polymer determines the release rate of the bioactive compound to the surrounding tissue.

Methods of constructing polymers having desired degradation characteristics are generally known. For example, co-polymers of poly[bis(p-carboxyphenoxy) propane anhydride] and sebacic acid may be synthesized to yield desired biodegradation characteristics. Pure poly[bis(p-carboxyphenoxy) propane anhydride] has a relatively low erosion rate. Co-polymerizing sebacic acid with poly[bis(p-carboxyphenoxy) propane anhydride] increases the erosion rate. As sebacic acid content increases, the erosion rate may increase by a factor of several hundred. See Leong et al., *J. Biomed. Mat. Res.*, 19:941–955 (1985), incorporated herein by reference. Thus by altering the relative content of each of the components, co-polymers having the desired degradation characteristics may be synthesized.

Many biocompatible polymers are known, including several which are biodegradable. Several are described in Langer, *Science*, 249:1527–1532 (1990) and Langer and Moses, *J. Cell. Biochem.*, 45:340–345 (1991), both of which are incorporated herein by reference. Poly-L-lactide polymers degrade over a period of months under physiological conditions. Lactic acid-glycolic acid co-polymers are also well known biodegradable polymers. Other acceptable polymers may contain monomers of hydroxyethylmethacrylate, vinylalcohol, ethylene-vinylacetate, lactic acid, or glycolic acid.

Particularly useful polymers in the present invention are polyanhydrides of the general formula

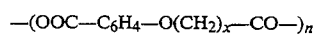

where x varies from 1 to 10 or

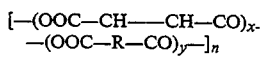

as generally described in Chasin et al., "Polyanhydrides as Drug Delivery Systems" in *Biodegradable Polymers as Drug Delivery Systems,* Langer and Chasin, eds. Mercel Dekker, Inc. 1990, pp. 43–70, incorporated herein by reference. Polymers comprising monomers such as carboxyphenoxyacetic acid, carboxyphenoxyvaleric acid, carboxyphenoxyoctanoic acid, terephthalic acid, and carbophenoxy propane-sebacic acid are examples of polymers acceptable for use in the present invention.

Polymers containing bioactive compounds may be formulated by a variety of methods well known in the art. For example, polymer matrices having the bioactive compounds incorporated within the matrices may be formulated by molding procedures. Briefly, polymer is ground and sieved to a desired particle size, usually about 90–150 μm. The bioactive compounds are ground and sieved to the same particle size and mixed with the polymer particles. The mixture is injection molded in commercially available molders. The polymer containing bioactive compounds is thus formed into strands and ready for weaving into the tubular member.

The strands may have a variety of cross-sectional shapes and dimensions which may be varied to control the release of the bioactive compound. Typically, the strands will have a circular cross-section although other cross-sectional shapes such as rectangular or ovoid are also acceptable.

The strands are woven through the perforations of the tubular member. At least one strand is woven through the perforations of each tubular member. Often multiple strands of different materials are woven through the perforations of each tubular member. Different strands may also contain different bioactive compounds. By placing different bioactive compounds in strands of different materials, stents of the present invention may be constructed which will release the different bioactive compounds at different rates, each in a controlled manner.

As an alternative to biodegradable polymers, the present invention can employ filaments of non-degradable materials which permit controlled release of the bioactive substances therefrom within the vascular environment. Suitable non-erodible polymers include styrene-divinyl benzene copolymer, methyl methacrylate-ethylene glycol and dimethylmethacrylate copolymer and ethylene-vinyl acetate copolymer. Filaments may be formed by extrusion of such copolymeric resigns, typically having dimensions in the range from about 0.04 mm to 0.4 mm.

The delivery matrix of the present invention is suitable for the delivery of a variety of pharmaceutical and other therapeutic agents including organic molecules, proteins, peptides, nucleotides, carbohydrates, polysaccharides, mucopolysaccharides, simple sugars, glycosaminoglycans, steroids and the like. The agents delivered may perform a variety of functions, including antithrombotic (e.g., lytic agents such as recombinant tissue plasminogen activator (TPA), urokinase and streptokinase), antiplatelet agents (aspirin, ticlopdine), inhibitors or surface glycoprotein receptors (e.g., GP IIb/IIIa, GP Ib-IX), antimetabolites (e.g. methotrexate), growth factor inhibitors, growth factor promoters, anticoagulants (e.g., heparin, low molecular weight heparins), direct thrombin inhibitors (e.g. hirudin and its derivatives, hirulog, thrombin aptamer, argatroban, D-phenylalanyl-L-poly-L-arginyl chloromethyl ketone), antimitotics (e.g., colchicine), antibiotics, antisense nucleotides, and the like.

Some embodiments of the present invention will comprise strands containing different bioactive substances or compounds. The strands containing the different bioactive compounds may be comprised of the same or different materials. When the strands are comprised of biodegradable polymers, use of a different polymeric formulation or a different polymer system provides a method of releasing the bioactive compounds at different rates. Alternatively, the same polymer may be used to provide for similar rates of release of different bioactive compounds.

Stents of the present invention may be useful in a variety of clinical settings. A common use of the present invention is for prevention of restenosis of coronary arteries following dilation of a stenotic arterial segment by transluminal procedures such as angioplasty. The intracoronary stents will generally have two types of biodegradable strands. An anticoagulant, usually heparin, will be contained within one strand. The heparin prevents thrombus formation caused by injury to the vessel during angioplasty or from foreign body reaction caused by the stent. The heparin containing strand degrades relatively quickly, usually within two to three weeks. This provides time for natural re-endothelialization to occur which will isolate the stent and injured vessel components from blood in the vascular space, and hence remove the thrombotic stimulus. The second strand will usually contain an antiproliferative agent such as methotrexate. The antiproliferative agent will inhibit over-proliferation of smooth muscle cells and thus inhibit re-stenosis of the dilated segment of the vessel. The antiproliferative containing strand will generally degrade over a period of four to six months. The physical presence of the stent will also inhibit re-stenosis of the vessel. In some applications the stents may have a third strand which contains a vasodilator such as a calcium channel blocker or a nitrate. The vasodilator will suppress vasospasm which is common following angioplasty procedures. The vasospasm occurs as a response to injury of the vessel. As the vessel heals, the tendency toward vasospasm decreases. The vasodilator strand will generally degrade in about two to three weeks. Stents may be placed in other blood vessels, such as the aorta, carotid arteries, renal, iliac, or peripheral arteries for similar purposes.

Stents of the present invention have other uses also. Stents of the present invention may be employed to provide controlled release of compounds to localized areas. For example, arterio-venous malformations may be treated by placement of a stent of the present invention. The stent will generally have one strand type which contains an irritant that naturally induces inflammation and fibrosis. On such irritant is tetracycline which can irritate the blood vessel leading to the malformation causing thrombosis and fibrotic closure of the malformation.

Stents of the present invention may also be used to deliver relatively high doses of anti-cancer chemotherapeutic agents to a localized tumor. For example, stents may contain several different strands containing different chemotherapeutic agents. The stents may be placed in the artery supplying blood to the tumor. The tumor can then be treated with relatively high and prolonged doses of the chemotherapeutic agents while limiting systemic toxicity. The stent may be used as a curative treatment, for pre-operative debulking, or for palliation of symptoms.

In another embodiment neurological disorders such as Parkinson's disease may be treated with stents of the present invention. In Parkinson's disease, dopamine of dopamine agonists, such as bromocriptine mesylate or pergolide mesylate, may be the bioactive compounds contained in biodegradable strands. The stents may be placed in the vascular supply of the thalamic substantia nigra. As the strands erode, the bioactive compound is released and flows into the substantia nigra providing localized treatment of the thalamus.

The stents of the present invention may also find use in body lumens other than blood vessels. One example is to preserve the integrity of the common bile duct in patients having primary cholangiosarcoma, secondary invasion of the duct by other tumors, or stone disease. Stents having strands containing antiproliferative agents may be placed in the common bile duct to prevent stenosis or restenosis resulting from malignancies such as pancreatic cancer. The stent may also find use in the treatment of genito-uretal disorders involving organs such as the prostate (benign prostatic hypertrophy or carcinoma via the prostatic urethra), penis (strictures via the penile urethra), fallopian tubes and the like. Persons of skill will appreciate that the stents of the present invention may be used in a wide variety of other clinical situations.

Stents of the present invention will generally not require open surgical placement. For example, stents to prevent restenosis of coronary arteries will generally be placed by transluminal angioplasty catheters. Generally, following angioplasty the stent will be directed to the dilated site by a balloon catheter. The stent, will be securely placed over the balloon. When the stent is within the dilated segment, the balloon will be inflated and the stent will expand to securely contact the vessel wall. As the balloon deflates, the stent retains its expanded form and remains securely in contact with the vessel wall. The deflated balloon can be withdrawn from the interior of the stent, leaving the stent in place. Placement of stents of the present invention in other locations may be similarly achieved. Alternatively, stents may be placed during open surgical procedures and perform similar functions.

Methods for preventing stenosis or restenosis of bodily fluid lumens are also provided. Hereinafter, the phrase "bodily fluid lumens" refers to body cavities which contain or transmit body fluids. This includes, but is not limited to, both arterial and venous blood vessels, the common and cystic bile ducts, the ureters, the urethra, central nervous system ventricles, and the like. Segments of bodily fluid lumens which have been dilated or which are at risk for stenosis may be protected from occlusion by inserting a stent comprising a tubular member having a radius, a first end, a second end, and a wall surface defining an interior of the tubular member, wherein the wall surface contains a plurality of perforations which allow the radius of the tubular member to be expanded by an outwardly expanding force from the interior, and an anti-proliferative compound contained in at least one first strand woven through perforations in the wall surface, into the dilated luminal segment; and expanding the stent to circumferentially contact the wall of the dilated segment of the lumen.

The method of lumen dilation is not critical and may vary. Generally stents of the present invention will be placed in dilated lumen segments by closed procedures, such as by placement by percutaneous transluminal angioplasty catheters in coronary arteries or by endoscopic placement in the common bile duct. Alternatively, the stents may be placed in lumen segments which have been surgically enlarged, e.g., placement in arteries following endarterectomy procedures.

The stent is positioned in the lumen so that the first end and the second end of the tubular member extend past the dilated lumen segment. In some embodiments of the present invention, an outward force is applied to the interior wall surface of the tubular member causing the tubular member to radially expand. The tubular member contacts the interior wall of the lumen. The pressure applied to the interior wall of the lumen by the tubular member may be controlled by controlling the amount of force applied to the interior of the tubular member. Conveniently, the force is applied by a inflation of a balloon catheter, such as an angioplasty catheter, within the tubular member. Following expansion of the tubular member, the balloon is deflated and withdrawn. The stent is held in place by the pressure of the tubular member on the interior wall of the lumen. While stents of the present invention will generally be placed following dilation of a stenotic segment, the stent may be placed in the stenotic segment and expanded simultaneous to dilating the stenotic segment.

In an alternative embodiment, the stent will be self-expanding and have elastic properties. The tubular member will be contracted and placed within the distal end of a catheter having a means to expel the stent from the distal end. Contraction of the stent causes outward tension in the tubular member, so that upon expulsion from the catheter the tubular member will radially expand and contact the lumen wall. Following expulsion of the stent, the catheter may be withdrawn. The outward tension of the tubular member will hold the stent in position in the lumen.

The present invention also provides methods for localized delivery of a bioactive compound to the interior of a body lumen. Localized delivery of bioactive compounds is useful in many clinical settings which determine the choice of bioactive compound contained in the stent. Localized delivery of antiproliferative agents is particularly useful for the treatment of a variety of malignant conditions characterized by highly vascular growth. In these instances, stents of the present invention may be placed in the arterial supply of the tumor to provide a means of relatively high dose delivery of the antiproliferative agent to the tumor. Generally the methods comprise inserting a stent comprising a tubular member having a radius, a first end, a second end, and a wall surface defining an interior of the tubular member, wherein the wall surface contains a plurality of perforations which allow the radius of the tubular member to be expanded by an outwardly expanding force from the interior, and at least one strand which contains the bioactive compound is woven through perforations in the wall surface; and expanding the stent to circumferentially contact the wall of the lumen. Placement of the stent is similar to the methods described above.

Reference will now be made to the figures. Uniform reference numbers will be used for corresponding elements in different figures. It will be understood that no limitation of the scope of the invention is intended and the figures are for illustrative purposes only. Alterations and modifications of the stents illustrated in the figures are contemplated to be within the scope of the invention.

In FIGS. 1A–1C, a stent 2 constructed in accordance with the principles of the present invention is shown. FIG. 1A illustrates a perspective view of the entire length of the stent 2 prior to expansion. The stent 2 is comprised of a tubular member 4. In this embodiment, the tubular member 4 is constructed from longitudinal elements 6 joined to form a tubular configuration by horizontal elements 8. Perforations 10 are formed by the spaces between the longitudinal elements 6 and horizontal elements 8. The tubular member 4 defines an interior 12 of the stent 2 which has a diameter d (see FIG. 1B).

As exemplified in FIG. 1C, the stent 2 contains two strands 14 and 16. The stands 14 and 16 are woven into the perforations 10 of the stent 2. The strands 14 and 16 are composed of different biodegradable polymers and contain different bioactive substances.

Figure 2A:
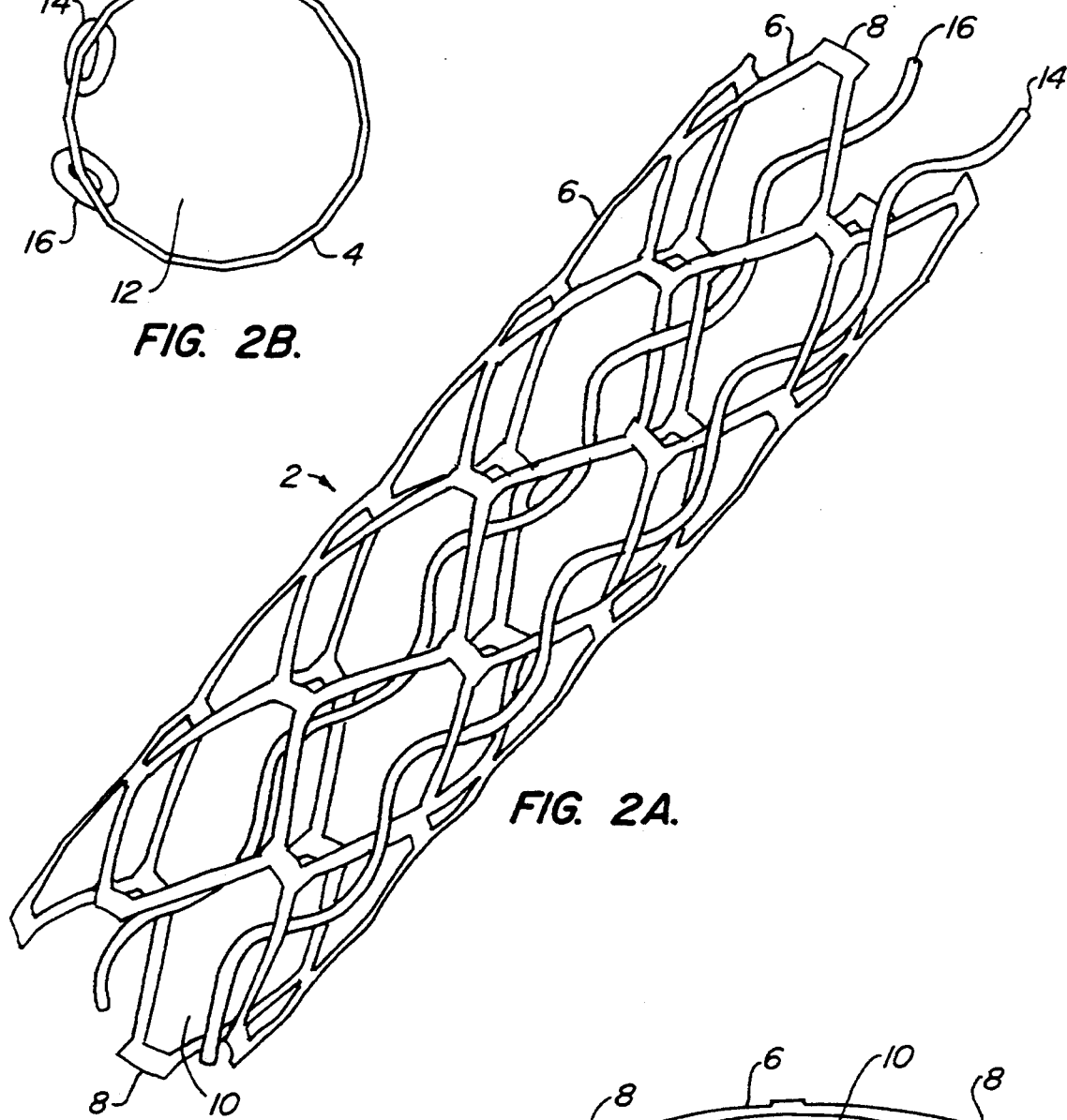
FIG. 2A illustrates a perspective view of a stent following expansion having two stands woven through the perforations.
Figure 2C:
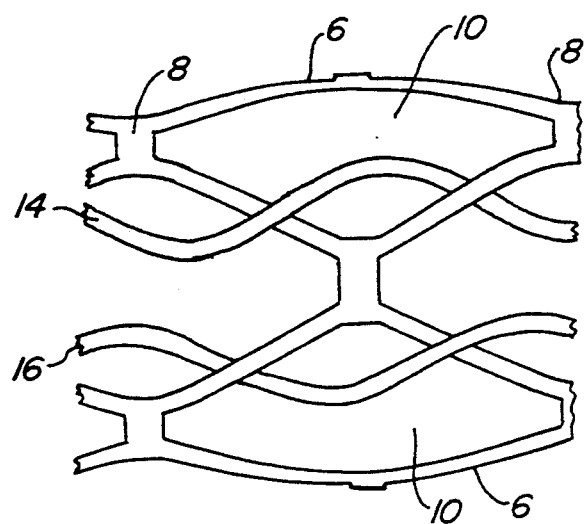
FIG. 2C illustrates a close-up perspective view of a stent having two strands woven through the perforations following expansion.

FIGS. 2A–2C illustrate the stent 2 of FIG. 1 following expansion. In FIG. 2A the longitudinal elements 6 have been deformed by the expansion. The longitudinal elements 6 remain joined by the horizontal elements 8. The perforations 10 have been widened by the expansion. The interior 12 of the stent 2 has an increased diameter d' which will provide for secure contact to be made between the tubular member 4 and the body lumen wall (See FIG. 2B).

As illustrated in FIG. 2C, the strands 14 and 16 remain woven through the perforations 10. Also, the strands 14 and 16 remain in close contact to the tubular member 4 so as to avoid obstruction of the interior 12 of the tubular member and to remain close to the body lumen wall.

Figure 3B:
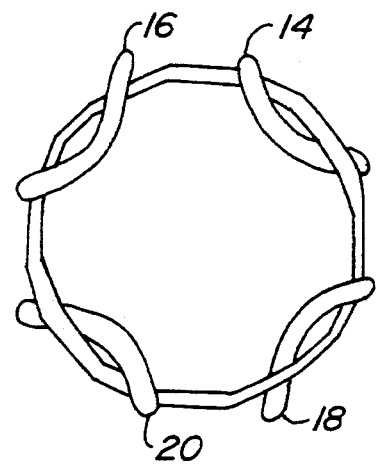
FIG. 3B illustrates a view through the interior of a stent following expansion having two pairs of strands woven through the perforations.
Figure 3A:
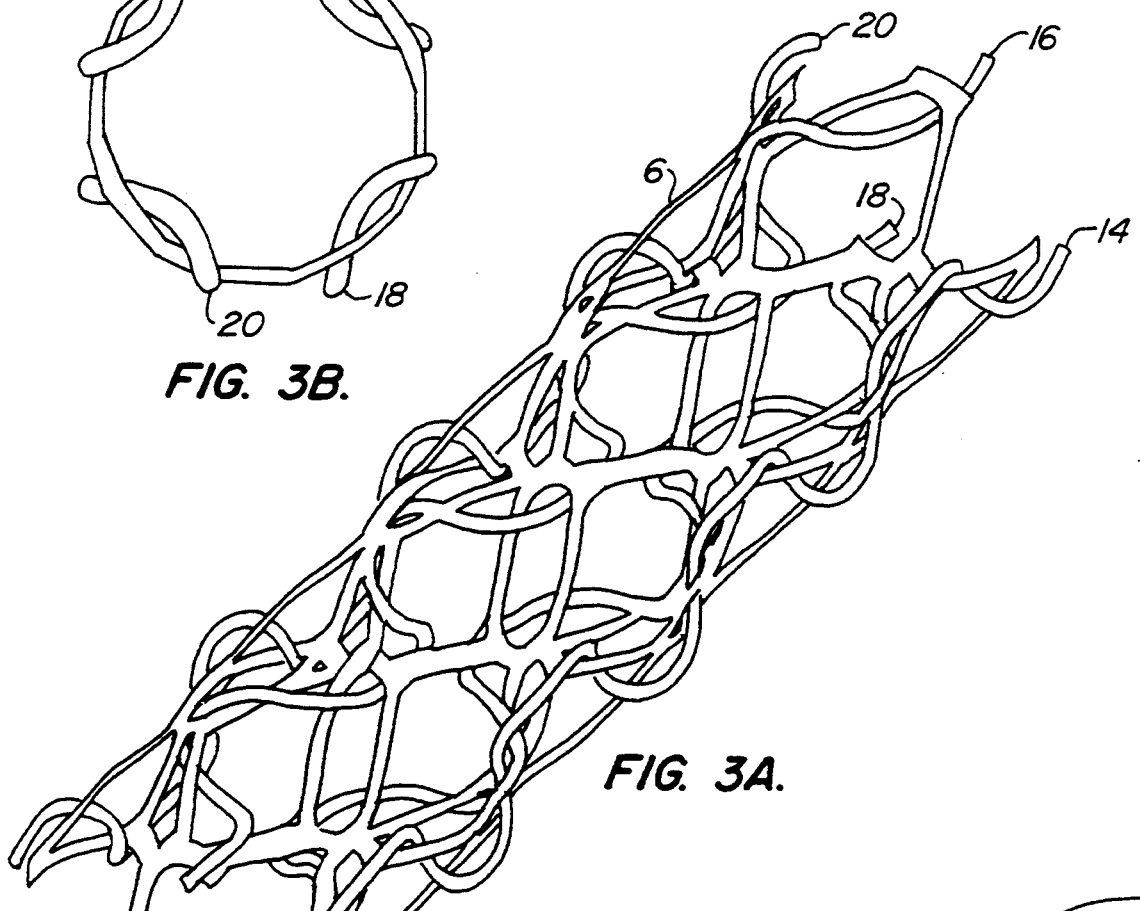
FIG. 3A illustrates a perspective view of a stent following expansion having two pairs of stands woven through the perforations.
Figure 3C:
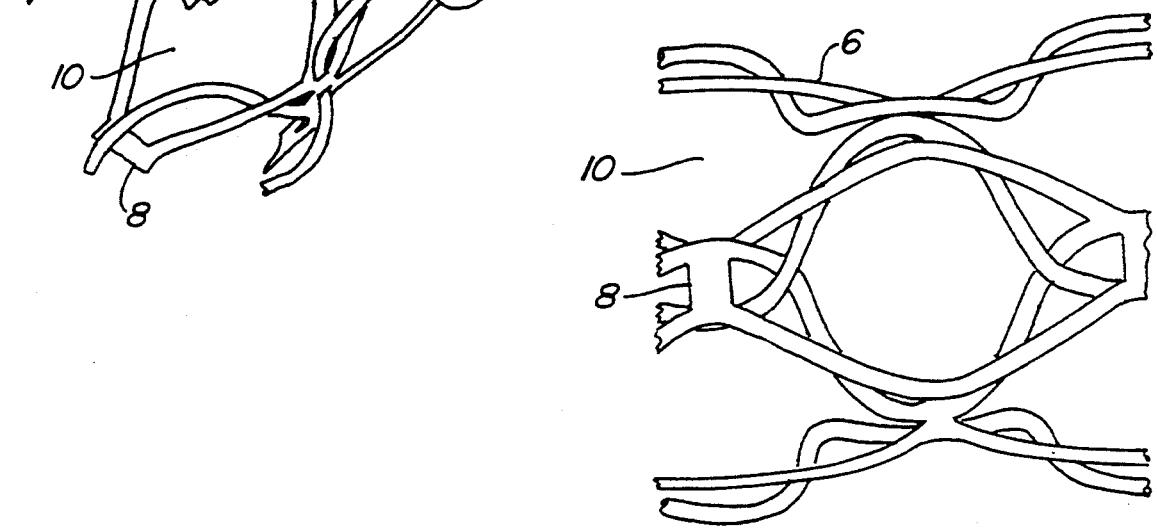
FIG. 3C illustrates a close-up perspective view of a stent having two pairs of strands woven through the perforations following expansion.

FIGS. 3A–3C illustrate one stent 2 of the present invention having four strands 14, 16, 18, and 20. The stent 2 is illustrated in an expanded configuration for clarity. Each of the strands 14, 16, 18, and 20 is woven through different perforations 10 in the tubular member 4. The four strands 14, 16, 18, and 20 provide for delivery of a greater amount of bioactive compound to a larger surface area of the lumen wall than stents having two strands of similar composition. Otherwise, the stent 2 functions similarly to stents with two strands.

Figure 4A:
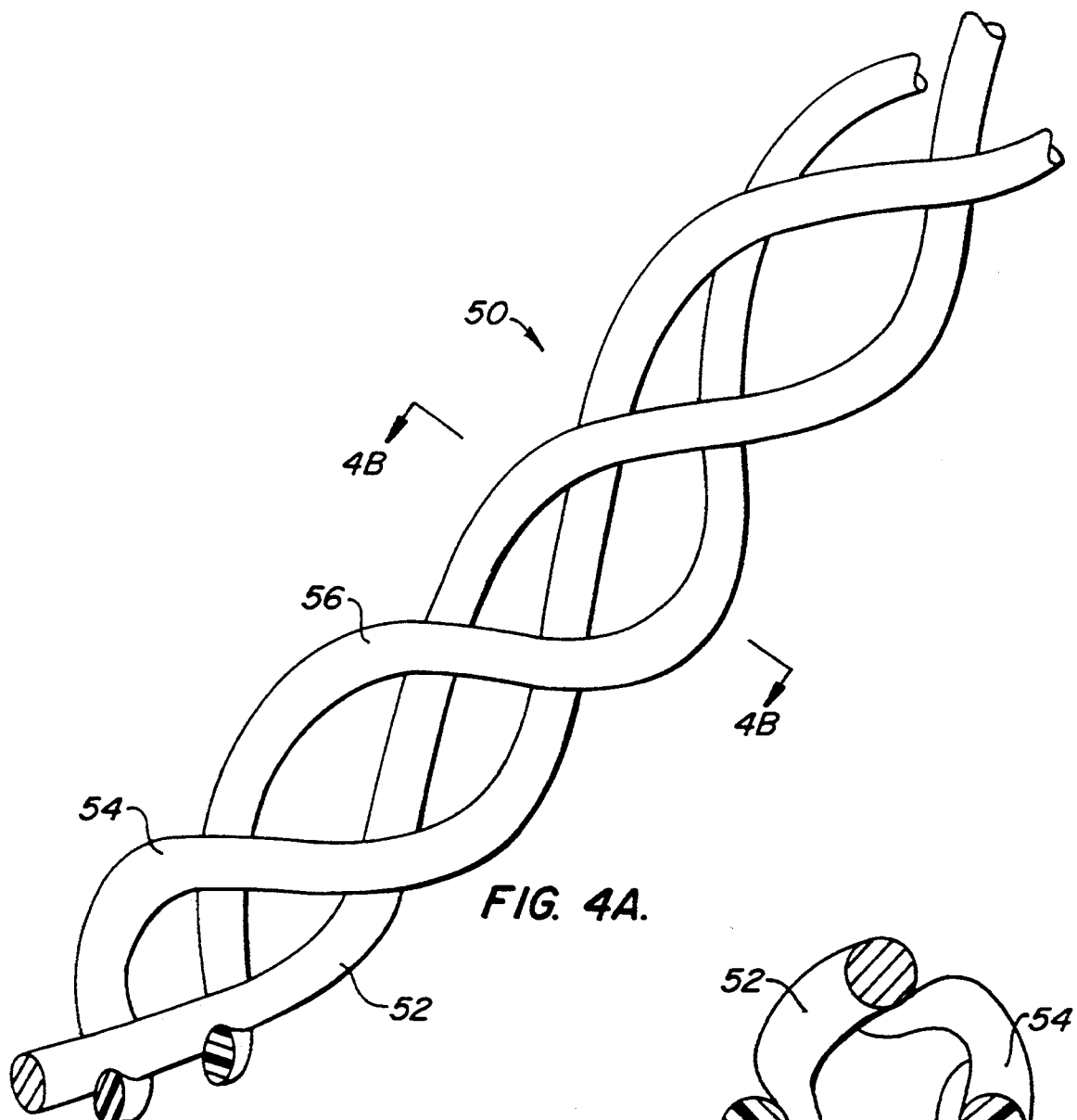
FIG. 4A illustrates a perspective view of a stent structure comprising a single helically wound strand and two counterwound delivery matrix filaments.
Figure 4B:
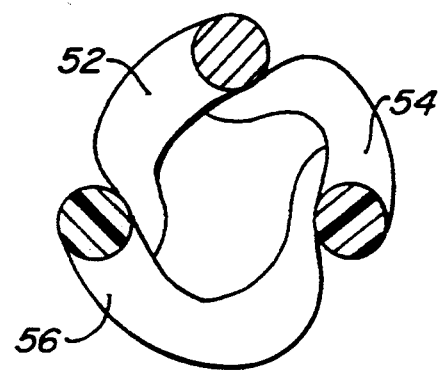
FIG. 4B is a cross-sectional view taken along line 4B—4B of FIG. 4A.

Referring now to FIGS. 4A and 4B, an alternative stent structure 50 comprising a helically wound strand 52 and a pair of counter-wound filaments 54 and 56 is illustrated. The strand 52 may be composed of either an elastic or a non-elastic material. Typically, strand 52 will be composed of a non-elastic, such as a biocompatible metal, which may be placed within the vascular system using balloon dilation catheter as described hereinafter in connection with FIG. 6A–6C. A strand 52 will typically be a wire having a circular cross-section, with a diameter of the range from about 0.05 to 0.25 mm.

The counter-wound delivery matrix filaments 54 and 56 may be composed of any of the materials described above, typically extruded or otherwise formed into elongate filaments which are counter wound and secured to the tubular strand 52 at crossing points. Securing may be achieved by adhesives, the application of heat, or the like.

Referring now to FIGS. 5A–5C, the second alternative structure 60 of the endovascular stent of the present invention will be described. The stent 60 also comprises a helical strand 62 which forms the tubular structure of the stent. The helical strand may be composed of an elastic or non-elastic material, as described generally above. Instead of counter-wound filaments, as described above for stent 50, stent 60 includes a laminated filaments 64, as best observed in FIGS. 5B and 5C. The filaments are composed of any of the materials described above for the delivery matrix filaments, which filaments are then laminated to the sides of the helical strand 62 by conventional techniques, such as adhesives, heat lamination, or the like. In the case of FIG. 5B, the strand 62 has a circular cross-section, and a pair of filaments 64 are shaped to conform to the concave surface presented by the strand. In the case of FIG. 5C, the strand 62' has a pair of flat opposed faces, and the filaments 64' are formed to secure to such flat faces.

Figure 6A:
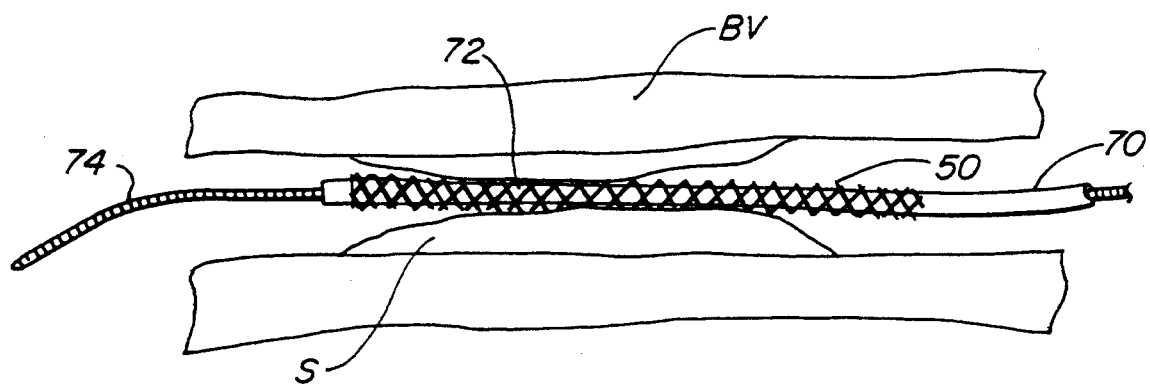
FIG. 6A–6C illustrate the method of the present invention for positioning the endovascular stent of FIGS. 4A and 4B in a blood vessel in order to deliver a bioactive substance therein. The stent is delivered with a balloon dilatation catheter and a stenosed region is dilated as a result of the procedure.
Figure 6B:
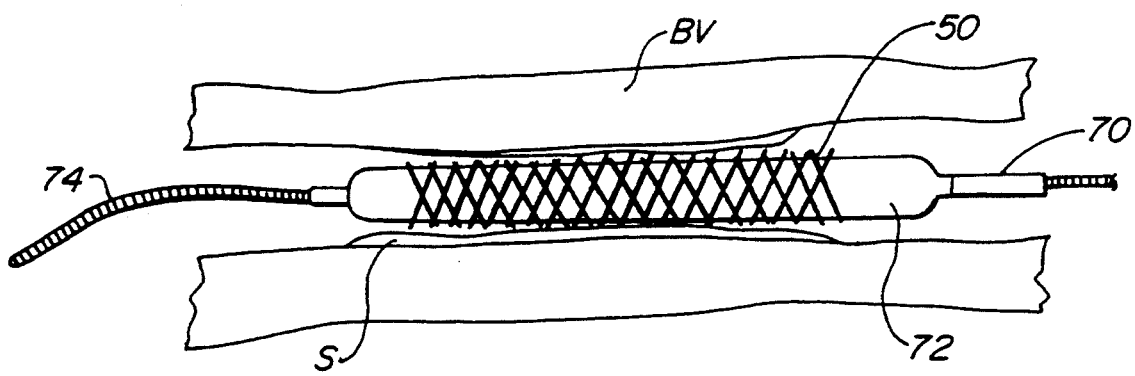
Figure 6C:
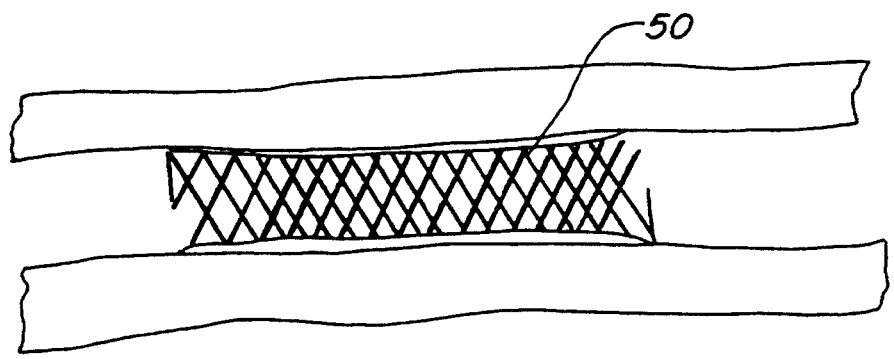

Referring now to FIGS. 6A–6C, a balloon dilitation catheter 70 may be used to deliver the stent 50 to region of Stenosis and a Blood Vessel. The stent 50 is initially carried in its initial (or reduced) diameter configuration on an uninflated balloon 72 of the balloon catheter 70. The balloon catheter is introduced over a conventional guidewire 74 and the stent 50 is positioned within the region of Stenosis using fluoroscopic imaging.

After the stent 50 is properly positioned within the region of Stenosis as illustrated in FIG. 6A, the balloon 72 will be inflated to expand the stent 50 within the region of Stenosis as illustrated in FIG. 6B. Stent 50 is composed of a non-elastic material, and will assume the enlarged configuration, as illustrated. The balloon 72 may then be deflated, and the catheter 70 may be withdrawn over the guidewire 74. After removal of the guidewire 74, the expanded stent 50 will be left in place, as illustrated in FIG. 6C. The stent 50 will provide for mechanical support of the dilated stenosed region, in a manner conventional for vascular stents. In addition, the stent 50 will provide one or more bioactive substances to the region immediately surrounding the region of dilation by releasing said substances from the filaments 54 and 56 (FIGS. 4A and 4B) of the delivery matrix of the stent. The materials of the delivery matrix can be selected to provide a desired bioactive substance delivery profile, with one or more bioactive substances being delivered at desired rates for desired time periods.

Although the foregoing invention has been described in detail for purposes of clarity of understanding, it will be obvious that certain modifications may be practiced within the scope of the appended claims.

What is claimed is:

1. An endovascular stent comprising:
    a tubular structure having an initial diameter, said structure being composed of a first material expandable from the initial diameter to an enlarged diameter;
    a delivery matrix including at least one filament which is interlaced with the tubular structure and expandable therewith from said initial diameter to said enlarged diameter; and
    a bioactive substance releasably contained within the filament of the delivery matrix, wherein the filament is composed of a second material which is porous and/or which will degrade over time in a vascular environment to release the bioactive substance.

2. The endovascular stent as in claim 1, wherein said tubular structure is composed of an elastic material, whereby the tubular structure may be constrained to said initial diameter and thereafter released to said enlarged diameter.

3. The endovascular stent as in claim 1, wherein said tubular structure is composed of a non-elastic material, whereby the tubular structure may be expanded from said initial diameter to said enlarged diameter.

4. The endovascular stent as in claim 1, wherein said tubular structure includes at least one helically wound strand, and wherein the filament of the delivery matrix is counter-woven with said helically wound strand.

5. The endovascular stent as in claim 1, wherein said tubular structure includes at least one helically wound strand, and wherein the filament of the delivery matrix is laminated over at least a portion of said helically wound strand.

6. The endovascular stent as in claim 1, wherein said tubular structure includes a perforated cylinder, and wherein the filament is interwoven through the perforations in said cylinder.

7. The endovascular stent as in claim 1, wherein the filament is composed of a material which is biodegradable within a physiologic environment whereby the bioactive substance is released as the filament erodes within a blood vessel.

8. The endovascular stent as in claim 7, wherein the filament material is composed of at least one polymer system selected from the group consisting of lactic acid/glycolic copolymer, carbophenoxy propane/sebacic acid, polycaprolactones, polyanhydride and poly ortho-esters.

9. The endovascular stent as in claim 1, wherein the filament is composed of a material which is substantially biodegradable within a physiologic environment and elutes bioactive substances.

10. The endovascular stent as in claim 9, wherein the material is composed of at least one polymer selected from the group consisting of silicone, ethylene-vinyl acetate copolymer, poly (vinylalcohol).

11. The endovascular stent as in claim 1, wherein the bioactive substance is selected from the group consisting of organic molecules, proteins, peptides, nucleotides, carbohydrates, polysaccharides, mucopolysaccharides, simple sugar, glycoaminoglycans and steroids.

12. The endovascular stent as in claim 1, wherein the first material is non-degradable in the vascular environment.

13. The endovascular stent as in claim 12, wherein the first material is selected from the group consisting of stainless steel, tantalum, gold, titanium, tungsten, platinum, polyether sulfone, polyamide, polycarbonate, polypropylene, high molecular weight polyethylene, and carbon fiber.

14. An endovascular stent comprising:
a tubular structure having an initial diameter, said structure being composed of a metal and being expandable from an initial diameter to an enlarged diameter;
a delivery matrix including at least one first filament and at least one second filament, which first and second filaments are composed of a polymeric material and interlaced with the tubular structure and expandable therewith from said initial diameter to said enlarged diameter; and
a bioactive substance releasably contained within both the first and second filaments wherein at least one of the first and second filaments is composed of a polymer material which will degrade over time in a vascular environment to release the bioactive substance and wherein the first and second filaments are composed of different materials.

15. The endovascular stent as in claim 14, wherein the first filament is composed of a first material selected to degrade and release the bioactive substance over a first time period and wherein the second filament is composed of a second material selected to degrade and release the bioactive substance over a second time period.

16. The endovascular stent as in claim 14, wherein the at least one filament material is composed of a least one polymer selected from the group consisting of lactic acid/glycolic copolymer, carbophenox propane/sebacic acid, polycaprolactones, polyanhydride and poly ortho-esters.

17. The endovascular stent as in claim 16, wherein both the first and second filaments are composed of the at least one polymer.

18. The endovascular stent as in claim 14, wherein one of the first and second filaments is composed of a material which is substantially non-biodegradable within a vascular environment which elutes substances.

19. The endovascular stent as in claim 18, wherein the non-biodegradable material is composed of at least one polymer selected from the group consisting of ethylenevinyl acetate copolymer, styrene-divinyl benzene copolymer, and methyl methacrylate-ethylene glycol copolymer.

20. A method for treating body lumens said method comprising:
inserting into the body lumen a stent comprising (i) a tubular structure composed of a first material having an initial diameter, (ii) a delivery matrix including at least one filament interlaced with the tubular structure, and (iii) a bioactive substance releasably contained within said filament; an d
expanding the stent at a location within the body lumen selected to be treated wherein the filament releases the bioactive substance from within under the conditions present the immediate environment.

21. The method as in claim 20, wherein the body lumen is a blood vessel and the selected location is a region of stenosis.

22. The method as in claim 21, wherein the bioactive substance is selected from the group consisting of organic molecules, proteins, peptides, nucleotides, carbohydrates, polysaccharides, mucopolysaccharides, simple sugar, glycoaminoglycans, and steroids.

23. The method as in claim 20, wherein the first material is non-degradable in the vascular environment.

24. The method as in claim 23, wherein the first material is non-degradable in the vascular environment.

* * * * *